United States Patent
Li et al.

(10) Patent No.: US 9,684,314 B1
(45) Date of Patent: Jun. 20, 2017

(54) GAS COLLECTION

(71) Applicant: The Board of Regents of the University of Nebraska, Lincoln, NE (US)

(72) Inventors: Haorong Li, Omaha, NE (US); Yanshun Yu, Nanjing (CN); Daihong Yu, Omaha, NE (US)

(73) Assignee: NUTECH VENTURES, Lincoln, NE (US)

( * ) Notice: Subject to any disclaimer, the term of this patent is extended or adjusted under 35 U.S.C. 154(b) by 839 days.

(21) Appl. No.: 13/936,129

(22) Filed: Jul. 5, 2013

Related U.S. Application Data (60) Provisional application No. 61/668,098, filed on Jul. 5, 2012.

(51) Int. Cl.
| | |
|---|---|
| *C12M 1/107* | (2006.01) |
| *C12M 3/00* | (2006.01) |
| *G05D 11/00* | (2006.01) |
| *G05D 11/04* | (2006.01) |
| *G05D 7/03* | (2006.01) |

(52) U.S. Cl.
CPC ............ *G05D 11/003* (2013.01); *G05D 7/03* (2013.01); *G05D 11/04* (2013.01)

(58) Field of Classification Search
CPC ......... G05D 11/003; G05D 7/03; G05D 11/04
See application file for complete search history.

(56) References Cited

U.S. PATENT DOCUMENTS

| | | | | |
|---|---|---|---|---|
| 6,162,556 | A * | 12/2000 | Vollmar | H01M 8/0612 429/411 |
| 2006/0006055 | A1* | 1/2006 | Bonde | B01D 3/346 203/73 |
| 2010/0018228 | A1* | 1/2010 | Flammang | F25B 27/02 62/115 |
| 2012/0137977 | A1* | 6/2012 | Hermes | A01K 61/02 119/6.5 |

OTHER PUBLICATIONS

G. Irvine, E. R. Lamont, and B. Antizar-Ladislao; Energy from Waste: Reuse of Compost Heat as a Source of Renewable Energy; International Journal of Chemical Engineering; vol. 2010, Article ID 627930; 10 pages.

* cited by examiner

*Primary Examiner* — William H Beisner
*Assistant Examiner* — Danielle Henkel
(74) *Attorney, Agent, or Firm* — Daniel J. Honz; Advent, LLP (57) ABSTRACT

A system includes a vessel configured to couple with a gas source for drawing gas into the vessel. The vessel is also configured to receive liquid. The system includes an overflow port in fluid communication with the environment external to the vessel. The overflow port is configured to separate gas within the vessel from the external environment. The system also includes an overflow conduit having an end within the overflow port so that when gas pressure within the vessel increases, liquid is received by the overflow conduit. Another system includes a tank defining an air space for receiving gas generated during the biodegradation of biomass feedstock. The second system also includes an exhaust port, a first evaporator, a first condenser, an expansion valve, and a compressor. The second system also includes a heat exchanger, a second evaporator, and a second condenser.

3 Claims, 8 Drawing Sheets

GAS COLLECTION

CROSS-REFERENCE TO RELATED APPLICATIONS

The present application claims the benefit under 35 U.S.C. §119(e) of U.S. Provisional Application Ser. No. 61/668,098, filed Jul. 5, 2012, and titled "Gas Collection System," which is herein incorporated by reference in its entirety.

BACKGROUND

As energy prices, environmental pollution, population growth, waste generation rate, and concerns regarding greenhouse-gas emissions continue to rise worldwide, there is an increasing desire for renewable energy and alternative energy and waste treatment solutions.

SUMMARY

A system includes a vessel configured to couple with a gas source for drawing gas into the vessel. The vessel is also configured to receive liquid. The system includes an overflow port in fluid communication with the environment external to the vessel. The overflow port is configured to separate gas within the vessel from the external environment and sustain gas pressure within the vessel. The system also includes an overflow conduit having an end within the overflow port so that when gas pressure within the vessel increases, liquid is received by the overflow conduit. The liquid can be drained through the overflow conduit to a water recycling tank. In some embodiments, real-time gas volume within the system is obtained (e.g., by metering the water level in the water recycling tank).

A system includes a tank defining an air space for receiving gas (e.g., hot air) generated during the biodegradation (e.g., aerobic biodegradation) of biomass feedstock. The system also includes an exhaust port configured to exhaust the gas from the air space of the tank. The system further includes a first evaporator coupled with the exhaust port, a first condenser coupled with the first evaporator, an expansion valve coupled between the first evaporator and the first condenser, and a compressor coupled with the first condenser. The system also includes a heat exchanger disposed of the tank for exchanging heat with the biomass feedstock during the biodegradation of the biomass feedstock, a second evaporator disposed in the air space defined by the tank and coupled with the heat exchanger, and a second condenser coupled with the second evaporator.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

In 2009, more than two hundred and fifty (250) million tons of municipal solid waste (MSW) was generated. Over two-thirds of this waste was comprised of organic material. However, only about seven percent (7%) of the waste was composted to produce fertilizers and so forth. The majority of biomass waste is placed in landfills or incinerated. Biodegradation provides ecologically and/or environmentally friendly techniques for handling biomass solid wastes, such as organic MSW. For example, biomass biodegradation can reduce environmental effects of biomass wastes (e.g., by neutralizing carbon and/or reducing sulfur, nitrogen oxides, methane emissions, and so forth). Further, biodegradation of biomass solid waste can be used to produce bio-fertilizers, which can be used to promote healthy and fertile soils for improved agricultural productivity, food production, and so forth. Additionally, biogas generated during, for instance, anaerobic digestion of biomass can be used to provide heat and/or power. Still further, biodegradation can be used to conserve landfill space, reduce disposal costs of biomass waste, produce a useful end product, and so forth.

Figure 1A:
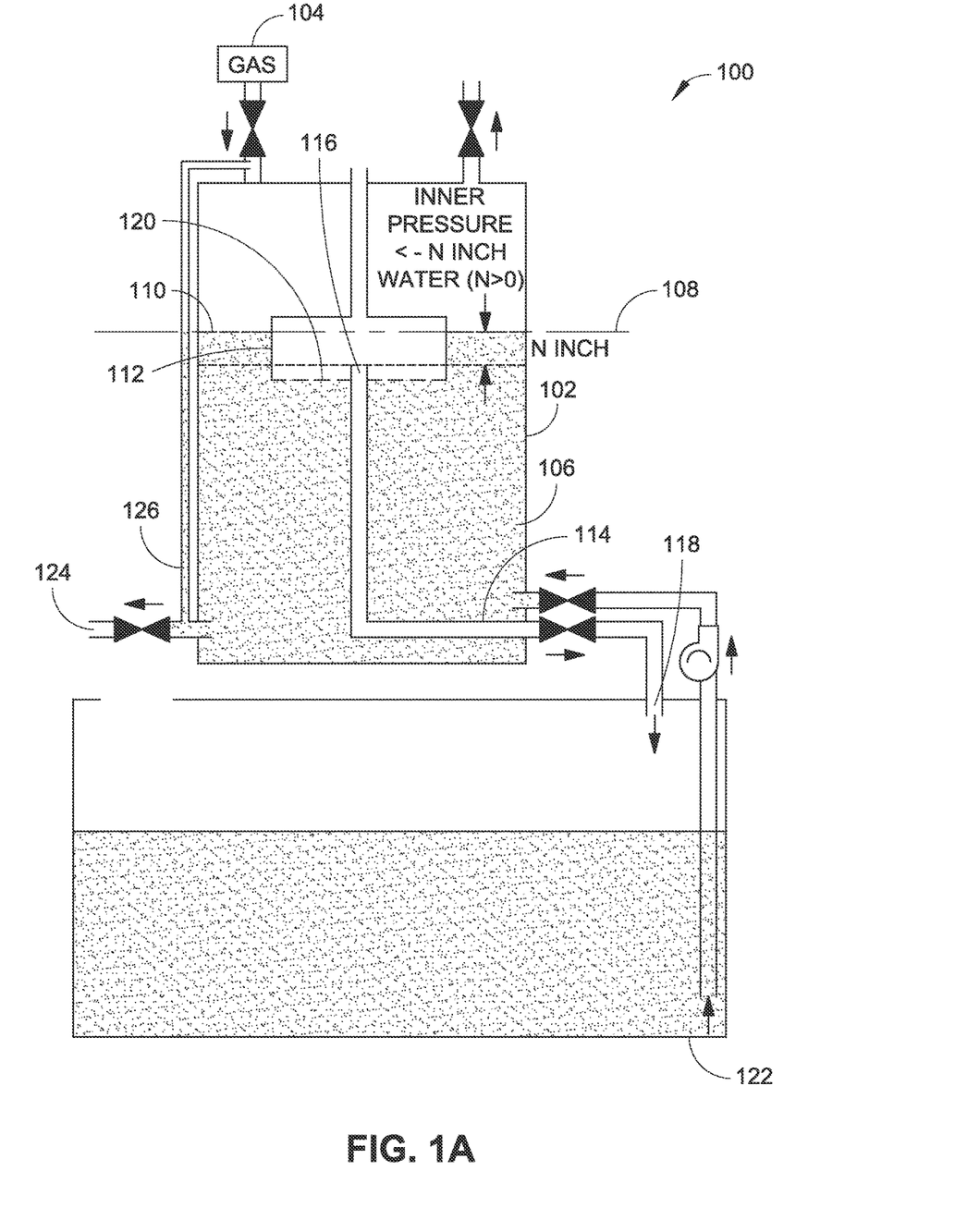
FIG. 1A is a diagrammatic illustration of a system configured to collect gas, such as biogas generated from the biodegradation of biomass waste, where an initial negative gas pressure is established within a vessel sealably coupled with a gas source in accordance with example embodiments of the present disclosure.
Figure 1B:
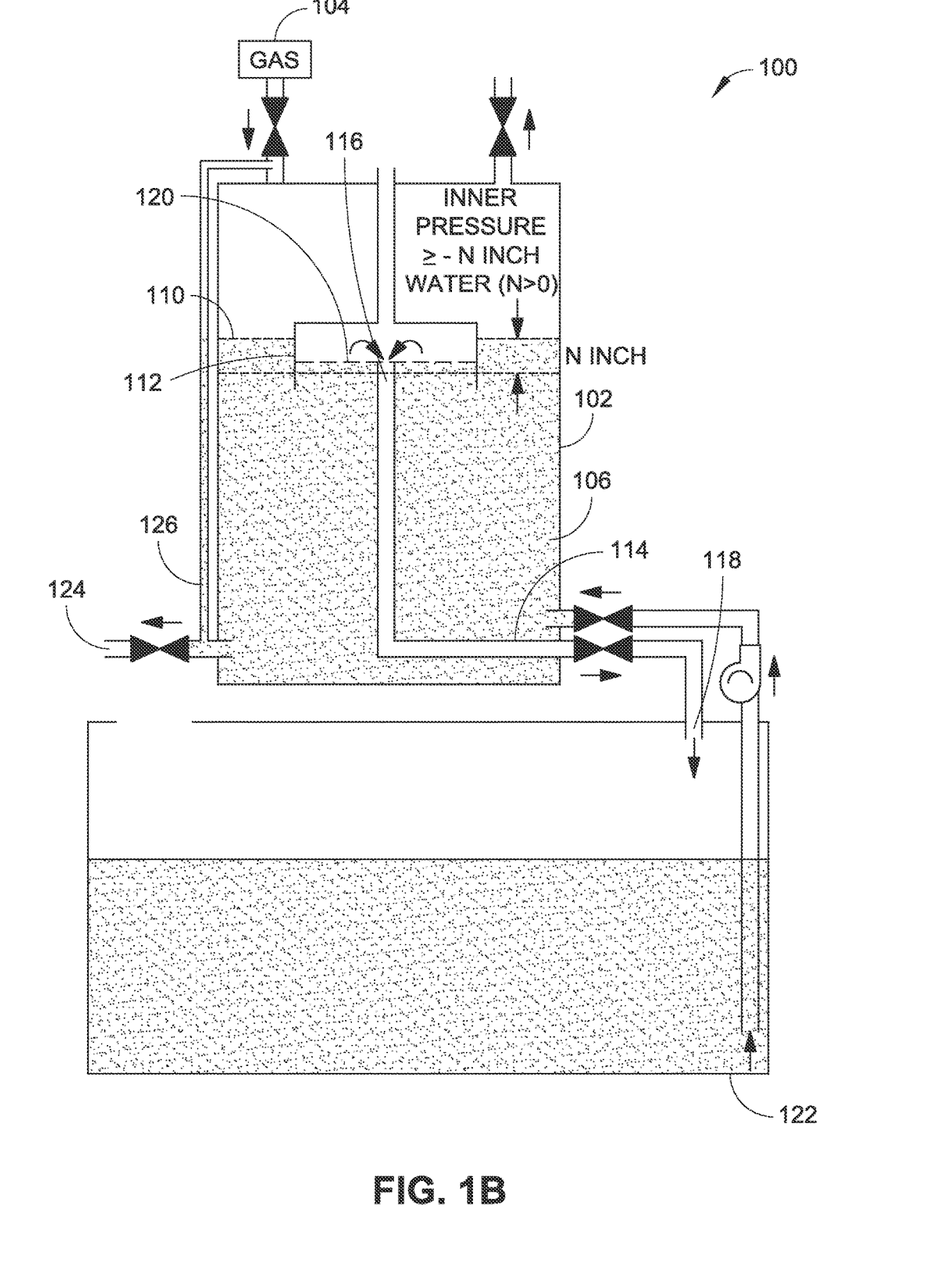
FIG. 1B is a diagrammatic illustration of the system illustrated in FIG. 1A, where the gas pressure within the vessel increases, and a portion of liquid in the vessel is received by an overflow conduit in accordance with example embodiments of the present disclosure.
Figure 2:
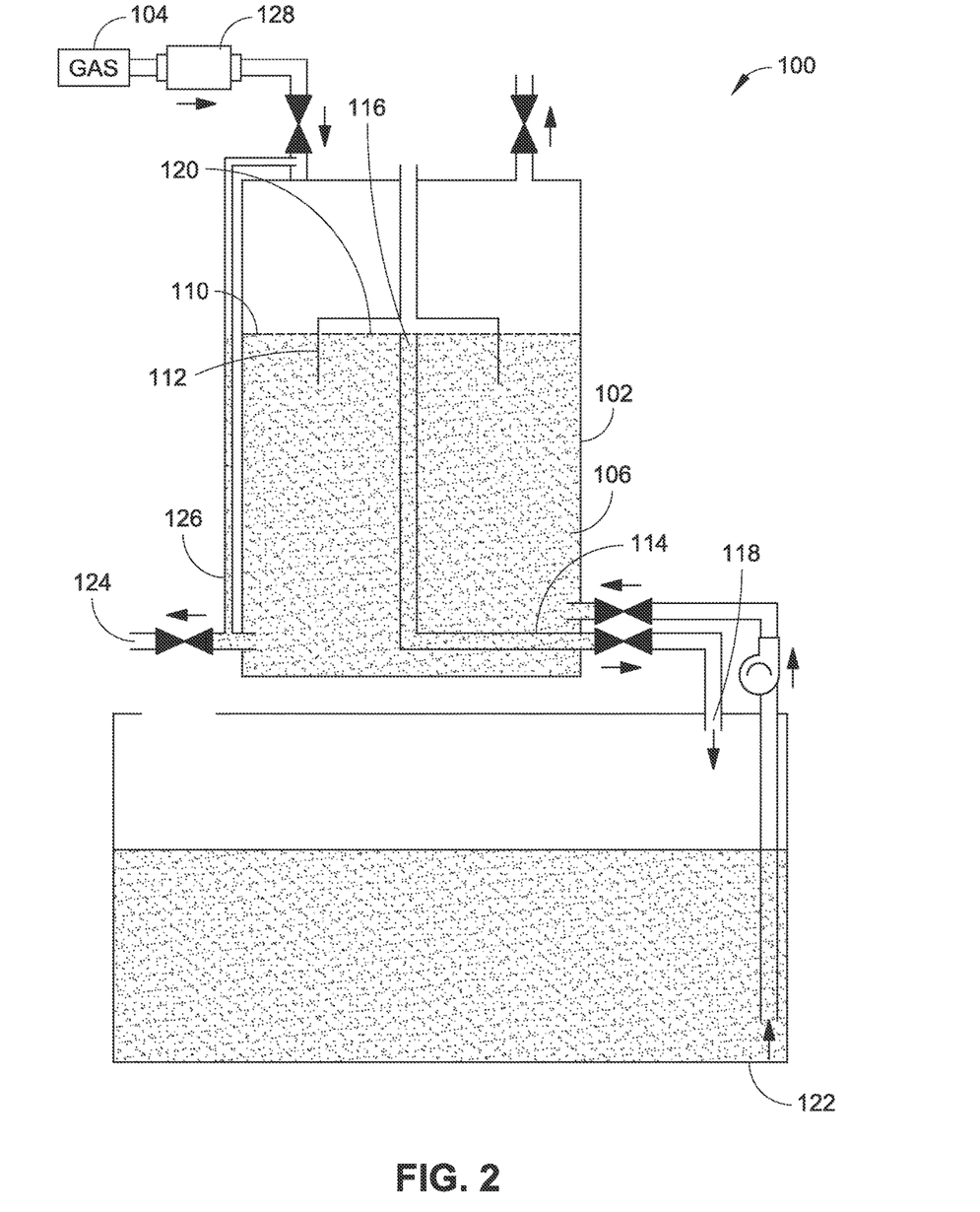
FIG. 2 is a diagrammatic illustration of another system configured to collect gas, such as biogas generated from the biodegradation of biomass waste, where an initial active gas pressure is established within a vessel sealably coupled with a gas source using a vacuum source in accordance with example embodiments of the present disclosure.

Referring generally to FIGS. 1A through 2, a system 100 for collecting gas, such as biogas generated from the biodegradation of biomass waste is described. The system 100 includes a vessel 102 configured to sealably couple with a gas source 104, such as a source of biogas from the biodegradation of biomass waste. As shown in FIG. 1A, an initial negative gas pressure is established within the vessel 102 with respect to the gas source 104 for drawing gas from the gas source 104 into the vessel 102. The vessel 102 is also configured to receive a liquid 106 (e.g., water) having an initial liquid level 108 at an interface 110 between the liquid 106 and the gas when the initial negative gas pressure is established within the vessel 102. The system 100 also includes an overflow port 112 in fluid communication with the environment external to the vessel 102 (e.g., via an atmospheric pressure conduit or the like). The overflow port 112 is configured to separate gas within the vessel 102 from the external environment. The system 100 further includes an overflow conduit 114 having a first end 116 and a second end 118. The first end 116 of the overflow conduit 114 is disposed within the overflow port 112 beneath the initial liquid level 108. In this manner, after the initial negative gas pressure is established within the vessel 102, when the gas pressure within the vessel 102 increases and a liquid level 120 in the overflow port 112 extends above the first end 116 of the overflow conduit 114, a portion of the liquid 106 is received by the overflow conduit 114.

In some embodiments, the system 100 includes a liquid reservoir 122 coupled with the vessel 102. In this configuration, the vessel 102 is configured to receive liquid 106 from the liquid reservoir 122, and the liquid reservoir 122 is configured to receive liquid 106 from the vessel 102 (e.g., when the gas pressure within the vessel 102 increases and the liquid level 120 in the overflow port 112 extends above the first end 116 of the overflow conduit 114). For example, the liquid reservoir 122 is coupled with the second end 118 of the overflow conduit 114 for receiving liquid 106 from the overflow conduit 114. In embodiments of the disclosure, the system 100 includes a liquid outlet 124 disposed proximate to the bottom of the vessel 102. In some embodiments, the system 100 includes a liquid level indicator 126 coupled between the vessel 102 and the gas source 104. In some embodiments, the system 100 includes a vacuum source 128 coupled with the vessel 102. The vacuum source 128 is configured to couple the vessel 102 with the gas source 104 for establishing the initial negative gas pressure within the vessel 102.

In embodiments of the disclosure, systems 100 implement fast, low-cost, scalable biomass waste anaerobic biodegradation systems that produce sustainable biogas energy and bio-fertilizers. The systems 100 use fast aerobic biodegradation technology as a pretreatment method to effectively break down complex compounds of biomass waste to readily biodegradable products, which can significantly increase the anaerobic biodegradation rate. Further the systems 100 can use multiple types of biomass wastes. In some embodiments, systems 100 provide a sustainable biogas yield rate of between approximately one and forty one-hundredths liters per day of liter-wet biomass (1.40 L/day·L-wet biomass) and one and eighty one-hundredths liters per day of liter-wet biomass (1.80 L/day·L-wet biomass). Further, in some embodiments the systems 100 provide a total volatile solids removal efficiency between approximately sixty percent (60%) and eighty percent (80%) within approximately ten (10) days. In this manner, biogas energy is generated for heat and/or power, reducing natural gas or electricity usage, minimizing capital investment, reducing resources usage for biogas energy plants, improving organic waste management, and/or quickly delivering healthy and fertile slurry.

The systems 100 provide low-cost, scalable, negative-pressure gas collection systems, which create a negative pressure condition within an anaerobic biodegradation system to effectively migrate the biogas into the collection system. The systems 100 can produce biogas energy, bio-fertilizers, and so forth.

Regarding concerns about odor complaints and environmental risks, gas collection technologies for effectively migrating explosive biogas from the anaerobic biodegradation systems are desirable. Currently, biogas is mainly collected by a passive or active-pressure gas collection system. However, these systems are often problematic, relatively inefficient, and/or relatively costly.

A passive-pressure gas collection system uses existing pressure variations in an anaerobic biodegradation system to vent biogas into control systems (e.g., flare, incinerators, boilers, gas turbines, and so forth). Thus, the efficiency of a passive-pressure biogas collection system generally depends on the overall biogas generation rate, and how the inner biogas release fittings of the anaerobic biodegradation system are implemented. Although the inner biogas release fittings can be lined throughout the anaerobic biodegradation system covering the top, bottom and sides of a container, biogas migration efficiency is not necessarily stable. Often, the biogas becomes trapped under the clay or geo-synthetic membranes of biomass feedstock with large-scale impermeable areas in the anaerobic biodegradation system, and biogas pressure is unable to push the gas into the collection system. Thus, biogas collection efficiency is reduced and anaerobic biodegradation is inhibited.

Typical active-pressure collection systems that use gas-moving equipment, like a vacuum, are relatively costly compared with a passive-pressure gas collection system. On the other hand, current gas collection systems, including both passive- and active-pressure collection systems, directly vent the biogas to control systems or the atmosphere. Further, these configurations lack stable sampling and analysis sub-collection systems for enabling ease of performance analysis.

Additionally, with passive-pressure gas collection systems, high barometric pressure can result in outside air entering the anaerobic biodegradation energy system through passive vents that are not routing gas to control devices. Consequently, with the oxygen mixed into the anaerobic biodegradation energy system, the biogas generation rate can be reduced significantly. These configurations provide slower degradation, longer retention time, larger energy systems, and greater capital investment, with smaller energy output. Thus, typical gas collection systems are often relatively inefficient, costly, and not considered reliable enough for use to vent biogas.

In order to migrate the biogas produced by the biomass waste anaerobic degradation system in a fast and stable manner, systems 100 implement low-cost, scalable, negative-pressure biogas or active-pressure collection systems using water displacement via the vessel 102 (e.g., a gas collection bucket), the liquid reservoir 122 (e.g., a water recycling tank), and possibly the vacuum source 128 (e.g., gas-moving equipment).

The systems 100 can be implemented using, for example, modular industrial components to ensure market-leading performance, scalability and service integration. The overflow port 112 implements an inner auto overflow structure (e.g., an inverted plastic bottle) within the gas collection bucket to create a negative pressure condition to effectively migrate the biogas from the anaerobic biodegradation system to the gas collection bucket. The inverted plastic bottle obtains atmospheric pressure for the space at the top and overflows the displaced water to the water recycling tank from the bottom at steady status. In some embodiments, gas-moving equipment (e.g., vacuum source 128) is used to create a low pressure condition to effectively migrate the biogas from the anaerobic biodegradation system to the gas collection bucket.

In the initial condition as shown in FIG. 1A, the inner pressure of the gas collection bucket is regulated to lower than −n inch water pressure (n>0), the water level in the inverted plastic bottle is lower than the inlet of the overflow conduit 114 (e.g., an overflow pipe). As biogas is created, inner pressure of the gas collection bucket increases to higher than −n inch water pressure, the water level in the inverted plastic bottle moves to higher than the inlet of the overflow pipe, the gas then displaces the water. The volume of gas can be determined by using the water level difference and the cross-sectional area of the gas collection bucket or the amount of water that is displaced by the gas for performance analysis. In addition, a water recycling tank is used to re-use and save the displaced water.

In this manner, the gas collection systems 100 migrate biogas produced from anaerobic biodegradation energy systems and generate environmental benefits, such as collecting the biogas in a fast, low-cost, and stable manner, and assisting the development of anaerobic biodegradation technology for producing biogas energy and bio-fertilizers; reducing environmental impacts from biogas emissions through the reduction of ozone precursors (volatile organic compounds and nitrogen oxides), methane, and odorous compounds; meeting government laws and regulations regarding operations and management of biogas production; and so forth.

Referring generally to FIGS. 3 through 7, a system 200 for recovering energy from biomass degradation (e.g., for supplying hot water, space heating, and so forth) is described. The system 200 includes a tank 202 (e.g., a reactor) configured to receive biomass feedstock for biodegradation. The tank 202 defines an air space 204 for receiving gas (e.g., biogas) generated during the biodegradation of the biomass feedstock. The system 200 also includes an exhaust port 206 coupled with the tank 202. The exhaust port 206 is configured to exhaust the gas generated during the biodegradation of the biomass feedstock from the air space 204 of the tank 202. The system 200 further includes a first evaporator 208 coupled with the exhaust port 206 for recovering heat from the exhaust gas. The system 200 also includes a first condenser 210 coupled with the first evaporator 208. In embodiments of the disclosure, an expansion valve 212 is coupled between the first evaporator 208 and the first condenser 210. The system 200 further includes a compressor 214 coupled with the first condenser 210. In some embodiments, the system 200 also includes a separator 216 for separating gas from liquid. The separator 216 is coupled between the compressor 214 and the first evaporator 208.

Figure 3:
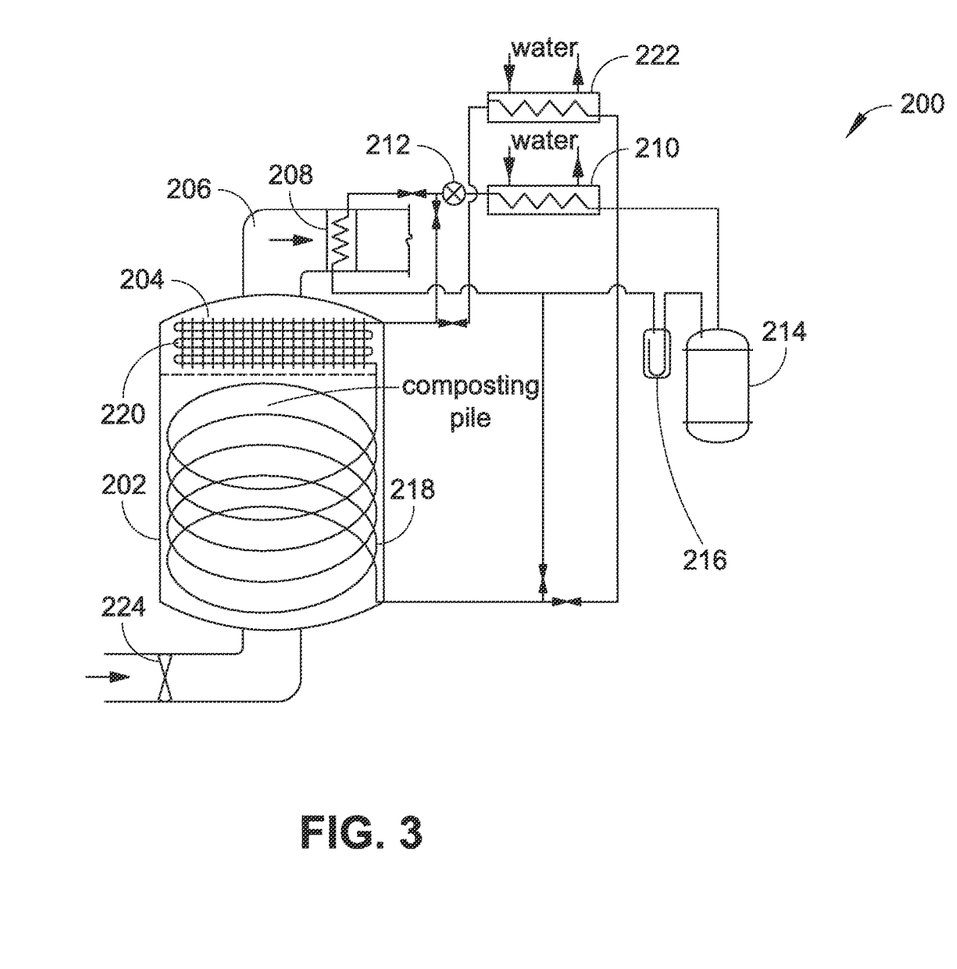
FIG. 3 is a diagrammatic illustration of a system implementing a heat pump for biomass energy recovery (e.g., for supplying hot water, space heating, and so forth) in accordance with example embodiments of the present disclosure.

The system 200 includes a heat exchanger 218 (e.g., a coil heat exchanger) disposed of the tank 202 for exchanging heat with the biomass feedstock during the biodegradation of the biomass feedstock. The system 200 also includes a second evaporator 220 disposed in the air space 204 defined by the tank 202. The second evaporator 220 is coupled with the heat exchanger 218 for recovering heat from the gas generated during the biodegradation of the biomass feedstock. The system 200 further includes a second condenser 222 coupled with the second evaporator 220. In some embodiments, the system 200 also includes a mechanical ventilator 224 (e.g., one or more fans) in fluid communication with the tank 202. The mechanical ventilator 224 is configured to supply air to facilitate the biodegradation of the biomass feedstock. For example, the system 200 includes an air supply grille allowing the mechanical ventilator 224 to draw inlet/supply air into the system 200.

Regarding energy consumption, buildings represent about thirty-nine percent (39%) of primary energy, seventy-four percent (74%) of electricity consumption, and thirty-nine percent (39%) of carbon emissions in the United States. Thus, effective waste management and renewable energy sources are important issues. However, typical waste treatment technologies have adverse effects on the environment, do not recycle useful materials, and/or do not reclaim the energy from waste. Generally, typical methods of solid waste treatment include landfills, mechanical heat treatment, and composting. The disposal of wastes in landfills generates methane that has a high global warming potential, while mechanical heat treatment requires specific facilities and may release undesirable gases. Thus, there is a need for effective mitigation of greenhouse gas emissions and reduction of residual containments, which could provide significant environmental benefits and sustainable development.

Composting is an effective method to handle municipal waste. Composting conserves landfill space, reduces disposal cost, and produces a useful end-product. There are large amounts of energy contained in wastes. For instance, gross calorific values (GCV) of kitchen wastes, papers and cards, and garden wastes are approximately fifteen and seven-tenths gigajoules per ton (15.7 GJ/t), seventeen and four-tenths gigajoules per ton (17.4 GJ/t), and sixteen and one-tenth gigajoules per ton (16.1 GJ/t), respectively. In the United States, there were about thirty-two and nine-tenths million tons (32.9 M tons) of yard trimmings in 2008, representing about two hundred trillion British thermal units (200 trillion Btu) of heat energy. Composting can be used for waste treatment and production of fertilizers from those organic materials.

Generally, with current practices of waste composting, heat is generated only as a byproduct of natural composting and is naturally released and not reclaimed. Temperature control is not considered in these systems. The systems 200 described herein provide waste-to-energy and waste treatment systems that can be implemented at the community level to recover heat from composting municipal wastes. The recovered heat can be used for supplying hot water, space heating, and so forth. In embodiments of the disclosure, the systems 200 are implemented for waste treatment, heat recovery, and/or production of fertilizers. Further, in some embodiments the systems 200 are used to recover between approximately fifty percent (50%) and seventy percent (70%) of the heat released by waste stabilization. The systems 200 can provide a sustainable heat output of between approximately ten watts per kilogram (10 W/kg) and fifteen watts per kilogram (15 W/kg) biomass on a wet basis.

A significant amount of heat generated from typical composting processes is discharged to the atmosphere by natural or mechanical ventilation. However, in some instances, about seventy-three percent (73%) of the theoretical energy value of the materials can be recovered. A complex biodegradation process is involved in composting, which reduces the volume and mass of solid organic wastes. Various microorganisms, populations, and mechanisms can be involved in composting different types of wastes.

As described, the system 200 includes the compressor 214, the expansion valve 212, the first and second evaporators 208 and 220, and the first and second condensers 210 and 222. The first and second evaporators 208 and 220 are used to recover the heat energy from the exhaust air, and from the air space in the tank 202 and the materials of the composting pile, respectively. While one condenser (i.e., the first condenser 210) is used for direct heat recovery from the exhaust air and the composting pile using heat pump technologies, another condenser (i.e., the second condenser 222)

can be installed at a higher level to implement a circuit of a heat pipe. In embodiments of the disclosure, high-temperature and high-pressure refrigerant from the compressor 214 is about primarily condensed in the first condenser 210 (e.g., for water heating).

In some embodiments, there are three operational modes for the system 200 according to the control strategies as described herein. In a first mode, heat-pump heat-recovery from exhaust air is implemented. In this mode, when the temperature of the composting pile is lower than a set point, the vapor-liquid refrigerant after the expansion valve 212 enters the evaporator 208 installed in the exhaust air duct of the exhaust port 206 to absorb the heat from the exhaust air. In this mode, the energy in the exhaust is recovered by the heat pump system 200.

In a second, combined heat-pump and heat-pipe mode, when the temperature of the composting pile is above another set point, the second condenser 222 and the second evaporator 220 in the composting pile form a heat-pipe circuit. This circuit is separated from the heat-pump system, and the refrigerant circulates inside the circuit due to different densities of refrigerants in the second evaporator 220 and the second condenser 222. In this manner, heat is removed from the composting pile to the second condenser 222 for water heating, and the temperature in the composting pile is controlled.

In a third, heat-pump heat-recovery from the exhaust and composting process mode, during the curing and manure stage of composting, the system 200 is operated to recover the heat in the exhaust air and the residual composting materials using the heat pump. In this mode, a portion of the vapor-liquid refrigerant after the expansion valve flows through the second evaporator 220 in the composting pile in order to absorb the heat from the residual compost.

Figure 4:
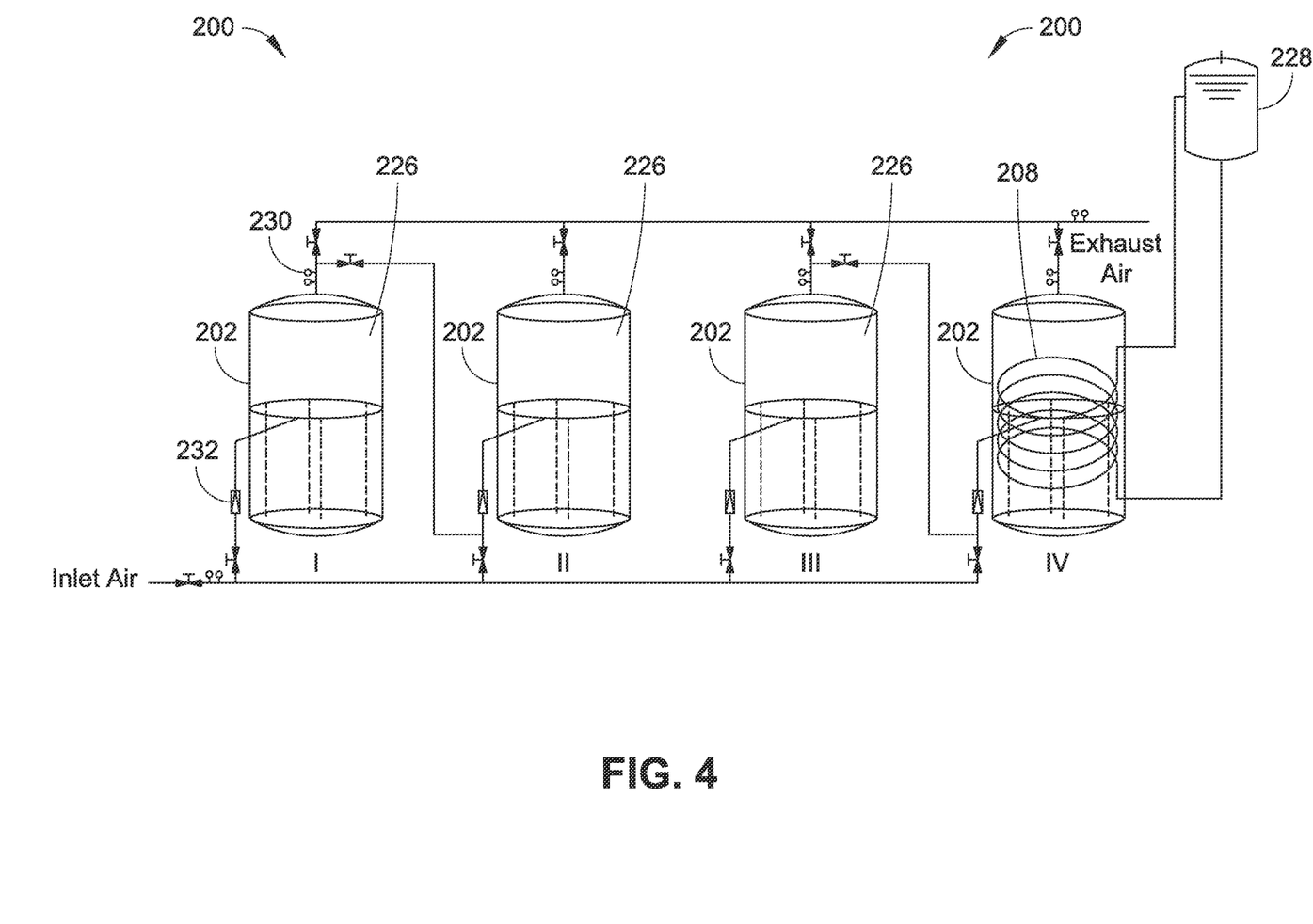
FIG. 4 is a diagrammatic illustration of a composting system configured for biomass energy recovery in accordance with example embodiments of the present disclosure.

With reference to FIG. 4, a system 200 is operated with yard grass clippings. The system 200 includes four tanks 202 (e.g., reactors), each approximately twenty and five-tenths (20.5) inches in diameter and twenty-seven (27) inches in height, with an effective volume of approximately thirty-two (32) gallons. An air distributor 226 is installed for each reactor to distribute air at least substantially uniformly and supply sufficient oxygen for composting. A heat exchanger 208 (e.g., a water exchanger with copper coils) is positioned inside the fourth reactor to recover the heat generated by biomass degradation and control the temperature of the compost pile. The water is cycled in a circuit comprising a water tank 228 and the coils of the water exchanger by differences in water density. In the system 200, the second and fourth reactors can also be operated to reuse the spent air of the first and third reactors by controlling valves installed in circulating air ducts. In embodiments of the disclosure, the system 200 also includes one or more temperature and/or humidity sensors 230 and/or a rotameter 232.

Figure 5:
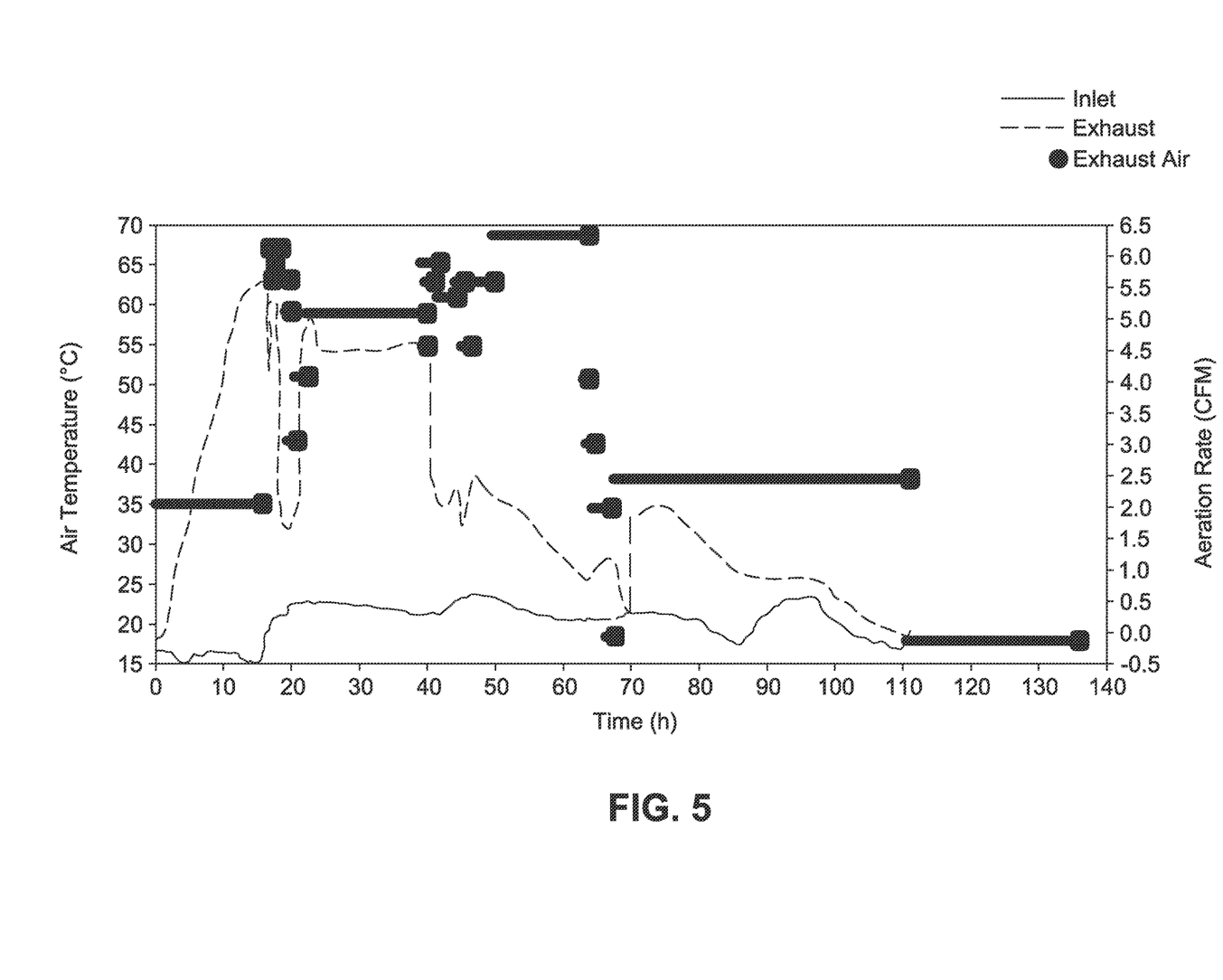
FIG. 5 is a graph illustrating exhaust and inlet air temperatures for a composting system configured for biomass energy recovery, such as the composting system illustrated in FIG. 4, in accordance with example embodiments of the present disclosure.
Figure 6:
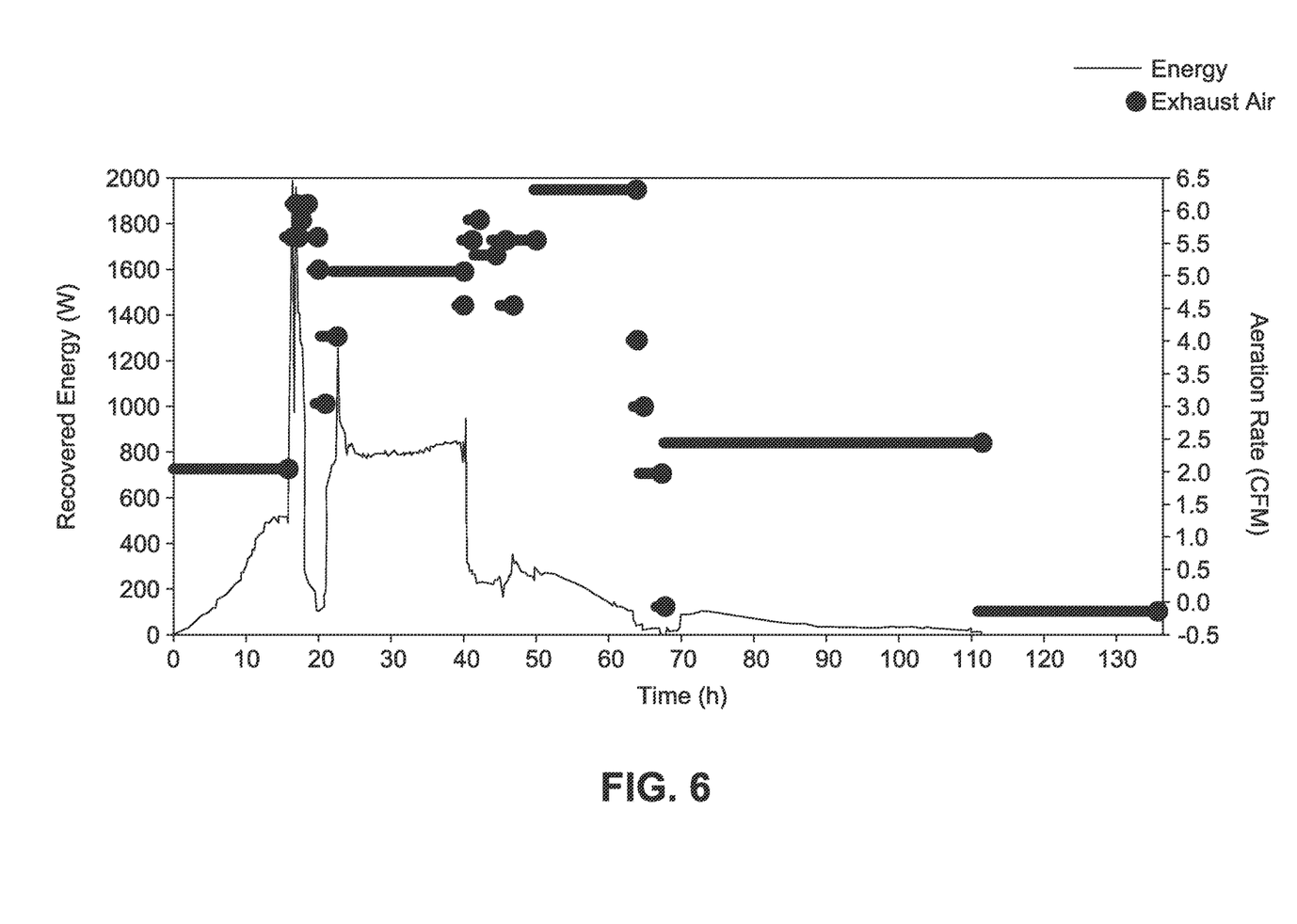
FIG. 6 is a graph illustrating recovered energy from biomass degradation for a composting system, such as the composting system illustrated in FIG. 4, in accordance with example embodiments of the present disclosure.
Figure 7:
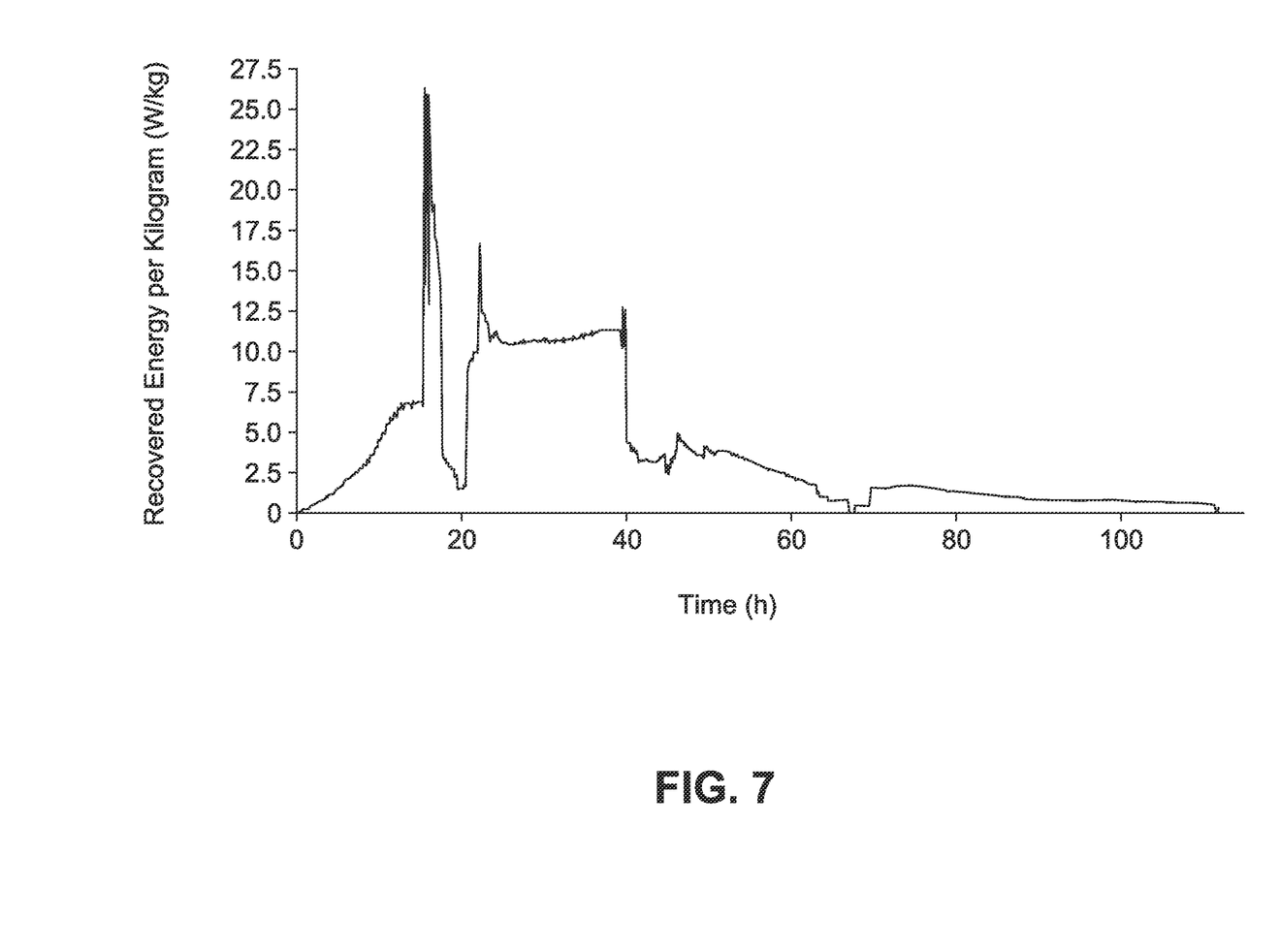
FIG. 7 is a graph illustrating recovered energy per kilogram of biomass for a composting system, such as the composting system illustrated in FIG. 4, in accordance with example embodiments of the present disclosure.

With reference to FIGS. 5 through 7, operational results of the system 200 illustrated in FIG. 4 are described. The total mass of the grass mixture for the four reactors is approximately one hundred six and five-tenths kilograms (106.5 kg), and the compost grass is mixed with approximately twenty-eight and five-tenths percent (28.5%) by weight old compost grass (inoculant) and approximately two and six-tenths percent (2.6%) by weight sawdust. The ratio of carbon-to-nitrogen (C:N) of the mixture is approximately thirty-nine to one (39:1), and the moisture content is approximately eighty percent (80%).

FIG. 5 illustrates the temperatures of inlet and exhaust air of the reactor system 200. The exhaust air temperature increases linearly at the beginning of the composting; after ten (10) hours, the temperature reaches fifty-five degrees Celsius (55° C.), and the peak temperature of the exhaust air is about sixty-five degrees Celsius (65° C.). Thus, the system 200 can be used as a heat source for a hot water supply, space heating in a building, and so forth. As illustrated in FIG. 6, during the high-temperature stage of composting, the maximum heat recovered from the grass composting is approximately one thousand nine hundred watts (1,900 W), lasting for approximately two (2) hours, and stabile recovered heat of approximately eight hundred watts (800 W) lasts for about twenty (20) hours. FIG. 7 illustrates the recovered energy per kilogram of initial compost mass on a wet basis. The peak recovered energy per kilogram biomass is about twenty-seven watts per kilogram (27 W/kg), and the relative stabile value of approximately ten and five-tenths watts per kilogram (10.5 W/kg) lasts for about twenty (20) hours.

The systems 200 described herein provide cost-effective solutions for solid organic waste treatment; effective mitigation of greenhouse gas emissions and reduction of residual containments; and environmental benefits and sustainable development. In 2008, the United States generated about two hundred fifty (250) million tons of trash and recycled and composted about eighty-three (83) million tons of this material, equivalent to about a thirty-three and two-tenths percent (33.2%) recycling rate. On average, one and five-tenths (1.5) pounds of individual waste generation of four and five-tenths (4.5) pounds per person per day was recycled and composted. For a four-member family, annual energy consumption is about $1.11836 \times 10^7$ British thermal units (Btu) and $2.87195 \times 10^7$ Btu for hot water supply and space heating, respectively. The average waste generation for a typical family is about eighteen (18) pounds per day. About sixty-five percent (65%) of this waste can be composted, and the heat release rate of composting is about ten watts per kilogram (10 W/kg), lasting for about one (1) week. This represents an energy consumption savings of about three thousand, two hundred and fifty-three kilowatt-hours per year (3,253 kWh/year). Further, the residue of composting is an excellent soil amending agent, and it can improve soil fertility and aeration conditions.

The system 100 and/or the system 200, including some or all of its components, can operate under computer control. For example, a processor can be included with or in a controller configured to control the components and functions of systems 100 and/or systems 200 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the systems 100 and/or the systems 200. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

A processor provides processing functionality for the system 100 and/or the system 200 and can include any number of processors, micro-controllers, or other processing systems, and resident or external memory for storing data and other information accessed or generated by the system 100 and/or the system 200. The processor can execute one or more software programs that implement techniques described herein. The processor is not limited by the materials from which it is formed or the processing mechanisms employed therein and, as such, can be implemented via semiconductor(s) and/or transistors (e.g., using electronic integrated circuit (IC) components), and so forth.

The system 100 and/or the system 200 also includes a memory. The memory is an example of tangible, computer-readable storage medium that provides storage functionality to store various data associated with operation of the system 100 and/or the system 200, such as software programs and/or code segments, or other data to instruct the processor, and possibly other components of the system 100 and/or the system 200, to perform the functionality described herein. Thus, the memory can store data, such as a program of instructions for operating the system 100 and/or the system 200 (including its components), and so forth. It should be noted that while a single memory is described, a wide variety of types and combinations of memory (e.g., tangible, non-transitory memory) can be employed. The memory can be integral with the processor, can comprise stand-alone memory, or can be a combination of both. The memory can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the system 100 and/or the system 200 and/or the memory can include removable integrated circuit card (ICC) memory, such as memory provided by a subscriber identity module (SIM) card, a universal subscriber identity module (USIM) card, a universal integrated circuit card (UICC), and so on.

The system 100 and/or the system 200 includes a communications interface. The communications interface is operatively configured to communicate with components of the system 100 and/or the system 200. For example, the communications interface can be configured to transmit data for storage in the system 100 and/or the system 200, retrieve data from storage in the system 100 and/or the system 200, and so forth. The communications interface is also communicatively coupled with the processor to facilitate data transfer between components of the system 100 and/or the system 200 and the processor (e.g., for communicating inputs to the processor received from a device communicatively coupled with the system 100 and/or the system 200). It should be noted that while the communications interface is described as a component of a system 100 and/or a system 200, one or more components of the communications interface can be implemented as external components communicatively coupled to the system 100 and/or the system 200 via a wired and/or wireless connection. The system 100 and/or the system 200 can also comprise and/or connect to one or more input/output (I/O) devices (e.g., via the communications interface) including, but not necessarily limited to: a display, a mouse, a touchpad, a keyboard, and so on.

The communications interface and/or the processor can be configured to communicate with a variety of different networks including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to be restrictive of the present disclosure. Further, the communications interface can be configured to communicate with a single network or multiple networks across different access points.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system comprising:
    a tank configured to receive biomass feedstock for biodegradation, the tank defining an air space for receiving gas generated during the biodegradation of the biomass feedstock;
    an exhaust port coupled with the tank, the exhaust port configured to exhaust the gas generated during the biodegradation of the biomass feedstock from the air space of the tank;
    a first evaporator disposed in the exhaust port for recovering heat from the exhaust gas;
    a first condenser coupled with the first evaporator;
    an expansion valve coupled between the first evaporator and the first condenser;
    a compressor coupled with the first condenser;
    a coil heat exchanger disposed in the tank for exchanging heat with the biomass feedstock during the biodegradation of the biomass feedstock;
    a second evaporator disposed in the air space defined by the tank, the second evaporator coupled with the heat exchanger for recovering heat from the gas generated during the biodegradation of the biomass feedstock; and
    a second condenser coupled with the second evaporator.

2. The system as recited in claim 1, further comprising a separator for separating gas from liquid, the separator coupled between the compressor and the first evaporator.

3. The system as recited in claim 1, further comprising a mechanical ventilator in fluid communication with the tank, the mechanical ventilator configured to supply air to facilitate the biodegradation of the biomass feedstock.

* * * * *